US007645873B2

(12) United States Patent
Savage et al.

(10) Patent No.: US 7,645,873 B2
(45) Date of Patent: Jan. 12, 2010

(54) 6"-AMINO-6"-DEOXYGALACTOSYLCER-AMIDES

(75) Inventors: Paul B. Savage, Mapleton, UT (US); Albert Bendelac, Chicago, IL (US); Luc Teyton, Del Mar, CA (US)

(73) Assignees: The Scripps Research Institute, La Jolla, CA (US); Brighman Young University, Provo, UT (US); The University of Chicago, Chicago, IL (US)

( * ) Notice: Subject to any disclaimer, the term of this patent is extended or adjusted under 35 U.S.C. 154(b) by 0 days.

(21) Appl. No.: 10/550,165

(22) PCT Filed: Mar. 20, 2003

(86) PCT No.: PCT/US03/08530

§ 371 (c)(1),
(2), (4) Date: Jul. 21, 2006

(87) PCT Pub. No.: WO2004/094444

PCT Pub. Date: Nov. 4, 2004

(65) Prior Publication Data

US 2006/0264382 A1 Nov. 23, 2006

(51) Int. Cl.
*A61K 31/7008* (2006.01)
(52) U.S. Cl. .......................................... 536/53; 514/23
(58) Field of Classification Search ................ 514/23; 536/53
See application file for complete search history.

(56) References Cited

U.S. PATENT DOCUMENTS

| 5,242,800 | A | 9/1993 | Jimenez et al. |
| 5,604,207 | A * | 2/1997 | DeFrees et al. ............... 514/25 |
| 5,767,092 | A | 6/1998 | Koezuka et al. |
| 5,780,441 | A | 7/1998 | Higa et al. |
| 5,785,975 | A | 7/1998 | Parikh |
| 5,849,716 | A | 12/1998 | Akimoto et al. |
| 5,936,076 | A | 8/1999 | Higa et al. |
| 5,958,426 | A | 9/1999 | Moreau et al. |
| 6,071,884 | A | 6/2000 | Koezuka et al. |
| 6,417,167 | B1 | 7/2002 | Maruyama et al. |
| 6,531,453 | B1 | 3/2003 | Taniguchi et al. |
| 6,610,835 | B1 | 8/2003 | Liotta et al. |
| 6,635,622 | B2 | 10/2003 | Tomiyama et al. |
| 6,747,010 | B2 | 6/2004 | Taniguchi et al. |
| 7,273,853 | B2 * | 9/2007 | Or et al. ...................... 514/29 |
| 2002/0115624 | A1 | 8/2002 | Behar et al. |
| 2003/0153514 | A1 | 8/2003 | Yagita |
| 2003/0157135 | A1 | 8/2003 | Tsuji et al. |
| 2004/0127429 | A1 | 7/2004 | Tsuji |
| 2004/0166554 | A1 | 8/2004 | Chamoles |
| 2004/0266726 | A1 | 12/2004 | Yagita |
| 2005/0192248 | A1 | 9/2005 | Tsuji et al. |
| 2005/0222048 | A1 | 10/2005 | Tsuji et al. |
| 2006/0019246 | A1 | 1/2006 | Tsuji et al. |
| 2006/0073118 | A1 | 4/2006 | Bendelac et al. |
| 2006/0211856 | A1 | 9/2006 | Tsuji et al. |
| 2008/0095787 | A1 | 4/2008 | Teyton |
| 2009/0047299 | A1 | 2/2009 | Savage |

FOREIGN PATENT DOCUMENTS

| EP | 0988860 | 3/2000 |
| EP | 1016409 | 7/2000 |
| WO | WO 99/33475 | 7/1999 |
| WO | WO 03/009812 | 2/2003 |
| WO | 03/018039 | 3/2003 |
| WO | WO 03/105769 | 12/2003 |
| WO | 2005/000348 | 1/2005 |
| WO | WO 05/102049 | 11/2005 |
| WO | WO 06/029010 | 3/2006 |
| WO | 2006/083671 | 8/2006 |
| WO | WO 07/050668 | 5/2007 |
| WO | 2007/118234 | 10/2007 |
| WO | 2008/005824 | 1/2008 |

OTHER PUBLICATIONS

Sinay, P. et al, Bioorganic and Medicinal Chemistry, 1998, 6, 1337-46.*
Zhou et al. "Synthesis and NKT Cell Stimulating Properties of Fluorophore- and Biotin-Appended 6 "-Amino-6"-deoxy-galactosylceramides." Organic Letters (2002) vol. 4, No. 8, pp. 1267-1270.
Benlagha, K. et al., "In Vivo Identification of Glycolipid Antigen-specific T Cells Using Fluorescent CD1d Tetramers," J. Exp. Med. (2000) 191:11:1895-1903.
Corey et al., "A New Method for the Synthesis of Organic Nitro Compounds," J. Am. Chem. Soc. (1984) 106:3682-3683.
Dascher, C.C. et al., "CD1 Antigen Presentation and Infectious Disease," Contributions to Microbiology (2003) 10:164-182.
Davis, N.J. et al., "Chemical Synthesis of Disaccharides Which are Partial Structures of the Glycosaminoglycan Heparan Sulfate," J. Chem. Soc. (1994) 1:359-368.
Hashimoto, S. et al., "Glycosylation Using Glucopyranosyl Fluorides and Silicon-Based Catalysts, Solvent Dependency of the Stereoselection," Tetrahedron Letters (1984) 25:13:1379-1382.
Hayashi, M. et al., "Simple Synthesis of Glycosyl Fluorides," Chem. Letters (1984) 1747-1750.
Kawano, T. et al., "CD1d-Restricted and TCR-Mediated Activation of Vα14 NKT Cells by Glycosylceramides," Science (1997) 278:1626-1629.
Khan, M. et al., "Syntheses and Antiinflammatory Activity of Some 6-aryl-2,3,4,5-tetrahydro-3-pyridazinones," Indian J. Chem. (2000) 39B:614-619.
Miyamoto, K. et al., "A Synthetic Glycolipid Prevents Autoimmune Encephalomyelitis by Inducing $T_H2$ Bias of Natural Killer T Cells," Nature (2001) 413:531-534.
Morita, M. et al., "Structure-Activity Relationship of α-Galactosylceramides Against B16-Bearing Mice," J. Med. Chem. (1995) 38:2176-2187.
Nakagawa, R. et al., "Mechanisms of the Antimetastatic Effect in the Liver and of the Hepatocyte Injury Induced by α-Galactosylceramide in Mice," J. Immun. (2001) 166:11:6578-6584.

(Continued)

*Primary Examiner*—Shaojia Anna Jiang
*Assistant Examiner*—Ganapathy Krishnan
(74) *Attorney, Agent, or Firm*—Merchant & Gould P.C.

(57) ABSTRACT

This invention relates to galactosylceramide compounds.

10 Claims, 1 Drawing Sheet

OTHER PUBLICATIONS

Pal, E. et al., "Costimulation-Dependent Modulation of Experimental Autoimmune Encephalomyelitis by Ligand Stimulation of Vα14 NK T Cells," J. Immunol. (2001) 166:662-668.

Park, S.H. et al., "The Mouse CD1d-restricted Repetoire is Dominated by a Few Autoreactive T Cell Receptor Families," J. Exp. Med. (2001) 8:893-904.

Park, S.H. et al., "CD1-Restricted T-Cell Responses and Microbial Infection," Nature (2000) 406:788-792.

Sakai, T. et al., "Effects of α- and β-Galactosylated C2-Ceramides on the Immune System," J. Med. Chem. (1998) 41:650-652.

Singh, P.P. et al., "The Synthesis of 2,3,4,6,7-Penta-O-Methyl-D-glycero-L-manno-Heptose and 2,4,6,7-Tetra-O-Methyl-D-glycero-L-manno-Heptose," Carbohydrate Res. (1970) 12:261-266.

Takikawa et al., "Diastereoselective Epoxidation of the Double Bond at C-4 of Sphinogosines to Provide Phytosphingosine Relatives such as α-Galactosylceramide KRN7000," Tetrahedron (1998) 54:3141-3150.

Vaultier, M. et al., Tetrahedron Letters (1983) 24:763 (Not In English).

Wang, B. et al., "CD1-Restricted NK T Cells Protect Nonobese Diabetic Mice from Developing Diabetes," J. Exp. Med. (2001) 194:313-319.

Wang, F. et al., "Tuning of Binding Selectivity: Metal Control of Organic Guest Binding and Allosteric Perturbation of Fluorescent Metal Sensor," J. Org. Chem. (1999) 64:8922-8928.

Weber, G. et al., "Synthesis and Spectral Properties of a Hydrophobic Fluorescent Probe: 6-Propionyl-2- (dimethylamino) naphthalene," Biochem. (1979) 18:14:3075-3078.

Beaudoin, L. et al., "NKT cells inhibit the onset of diabetes by impairing the development of pathogenic T cells specific for pancreatic beta cells," Immunity (2002) 17:725-736.

Bendelac, A. et al., "Autoreactivity by design: innate B and T lymphocytes," Natur. Rev. Immunol. (2001) 1:177-186.

Bendelac, A. et al., "The biology of NKT cells," Ann. Rev. Immunol. (2007) 25:297-336.

Bendelac, A., "Nondeletional pathways for the development of autoreactive thymocytes," Nat. Immunol. (2004) 5:557-558.

Brossay, L. et al., "Cutting edge: structural requirements for galactosylceramide recognition by CD1-restricted NK T cells," J. Immunol. (1998) 161(10):5124-5128.

Daoudi, J-M. et al., "New bicyclam-galcer analogue conjugates: synthesis and in vitro anti-HIV activity," Biorg. Med. Chem. Lett. (2004) 14:495-498.

De Libero, G. et al., "Self glycosphingolipids: new antigens recognized by autoreactive T lymphocytes," News Physiol. Sci. (2003) 18:71-76.

European Office Action for Application No. 05810863.0 dated Apr. 2, 2008 (4 pages).

Fischer, K. et al., "Mycobacterial phosphatidylinositol mannoside is a natural antigen for CD1d-restricted T cells," Proc. Natl. Acad. Sci. USA (2004) 101:10685-10690.

Goodman & Gilman's The Pharmacological Basis of Therapeutics, Tenth Edition, Hardman and Limbird, editors, The McGraw-Hill Companies, Inc., New York, (2001) 54-56.

Gumperz, J.E. et al., "Murine CD1d-restricted T cell recognition of cellular lipids," Immunity (2000) 12:211-221.

Gupta, R.K. et al., "Adjuvants—a balance between toxicity and adjuvanticity," Vaccine (1993) 11(3):293-306.

Honey, K. et al., "Thymocyte expression of cathepsin L is essential for NKT cell development," Nat. Immunol. (2002) 3:1069-1074.

International Search Report and Written Opinion for Application No. PCT/US2005/031407 (13 pages).

Islam, I. et al., "Synthesis and antiviral activity of (2-((4-(3-((1-methylethyl)amino)-2-pyridyl)-1- piperazinyl)carbony)-1H-indo 1-5-yl) (BHAP) acylspingosine HIV reverse transcriptase inhibitors," Biorg. Chem. (1995) 23(4):499-511.

Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," J. Exp. Med. (1999) 189:1121-1127.

Park, S.-H. et al., "Tissue-specific recognition of mouse CD1 molecules," J. Immunol. (1998) 160:3128-3134.

Prigozy, T.I. et al., "Glycolipid antigen processing for presentation by CD1d molecules," Science (2001) 291:664-667.

Smyth, M.J. et al., "NKT cells—conductors of tumor immunity?" Curr. Opin. Immunol. (2002) 14(2):165-171.

Smyth, M.J. et al., "NKT cells and tumor immunity—a double-edged sword," Nature Immunology (2001) 1:459-460.

Stanic A.K. et al., "Defective presentation of the CD1d1-restricted natural Va14Ja18 NKT lymphocyte antigen caused by Beta-D-glucosylceramide synthase deficiency," Proc. Natl. Acad. Sci. USA (2003) 100:1849-1854.

United States Office Action for U.S. Appl. No. 11/218,906 dated Nov. 10, 2008 (8 pages).

United States Office Action for U.S. Appl. No. 11/771,128 dated Oct. 29, 2008 (14 pages).

Van Der Vliet, H.J.J. et al., "Effects of α-galactosylceramide (KRN7000), interleukin-12 and interleukin-7 on phenotype and cytokine profile of human Vα24+Vβ11+T cells," Immunology (1999) 98:557-563.

Vandommelen, S.L.H. et al., "Activation of natural killer (NK) T cells during murine cytomegalovirus infection enhances the antiviral response mediated by NK cells," J. Virology (2003) 77(3):1877-1884.

Winau, F. et al., "Saposin C is required for lipid presentation by human CD 1b," Nat. Immunol. (2004) 5:169-174.

Wu, D.Y. et al., "Cross-presentation of disialoganglioside GD3 to natural killer T cells," J. Exp. Med. (2003) 198:173-181.

Xia, C. et al., "Thio-isoglobotrihexosylceramide, an Agonist for activating invariant natural killer T cells," Org. Lett. (2006) 8(24):5493-5496.

Zajonc, D.M. et al., "Structural basis for CD1d presentation of a sulfatide derived from myelin and its implications for autoimmunity," J. Exp. Med. (2005) 202(11):1517-1526.

Zhou, D. et al., "Editing of CD1d-bound lipid antigens by endosomal lipid transfer proteins," Science (2004) 303:523-527.

Zhou, D., "The immunological function of iGb3," Curr. Prot. Pept. Sci. (2006) 7:325-333.

Brutkiewicz, R.R. et al., "CD1d-mediated antigen presentation to natural killer T (NKT) cells," Critical Reviews in Immunology (2003) 23:403-419.

Brutkiewicz, R.R et al., "Natural Killer T (NKT) Cells and Their Role in Antitumor Immunity," Critical Reviews in Oncology/Hematology (2002) 41:287-298.

Singh, A.K. et al., "The Natural Killer T Cell Ligand Alpha-Galactosylceramide Protects Mice Against EAE by an IL-4-and IL-10-Dependent Mechansim," FASEB J., Fed. of Amer. Soc. for Exp. Bio. (2002) 16:A1043.

U.S. Appl. No. 11/814,103, Teyton et al.

Ando, H. et al., "Solid-phase capture-release strategy applied to oligosaccharide synthesis on a soluble polymer support," Angew. Chem. Int. Ed. (2001) 40:4725-4728.

Bendelac, A. et al., "Increased interleukin 4 and immunoglobulin E production in transgenic mice overexpressing NK1 T cells," J. Exp. Med. (1996) 184:1285-1293.

Brigl, M. et al., "Cd1: T cell function and antigen presentation," Annu. Rev. Immunol. (2004) 22:817-890.

Brigl, M. et al., "Mechanism of CD1d-restricted natural killer T cell activation during microbial infection," Nat. Immunol. (2003) 4:1230-1237.

Cantu, C. et al., "The paradox of immune molecular recognition of alpha-galactosylceramide: low affinity, low specificity for CD1d, high affinity for alpha beta TCRs," J. Immunol. (2003) 170:4673-4682.

Fujii, S-I. et al., "Activation of natural killer T cells by alpha-galactosylceramide rapidly induces the full maturation of dendritic cells in vivo and thereby acts as an adjuvant for combined CD4 and CD8 T cell immunity to a coadministered protein," J. Exp. Med. (2003) 198:267-279.

Garrity, G.M. et al., Taxonomic Outline of the Procaryotic Genera, Bergey's Manual of Systematic Bacteriology, 2nd Edition (Apr. 2001).

Godfrey, D.I. et al., "Going both ways: immune regulation via CD1d-dependent NKT cells," J. Clin. Invest. (2004) 114(10):1379-1388.

Godfrey, D.I. et al., "The elusive NKT cell antigen—is the search over?" Science (2004) 306:1687-1688.

Goff, R.D. et al., "Effects of lipid chain lengths in alpha-galactosylceramides on cytokine release by natural killer T cells," J. Am. Chem. Soc. (2004) 126:13602-13603.

Gui, M. et al., "TCR beta chain influences but does not solely control autoreactivity of V alpha 14J28IT cells," J. Immunol. (2001) 167(11):6239-6246.

Gumperz, J.E. et al., "Functional distinct subsets of CD1d-restricted natural killer T cells revealed by CD1d tetramer staining," J. Exp. Med. (2002) 195(5):625-636.

Hermans, I.F. et al., "NKT cells enhance CD4+ and CD8+ T cell responses to soluble antigen in vivo through direct interaction with dendritic cells," J. Immunol. (2003) 171:5140-5147.

Iida, N. et al., "A sulfated glucosylceramide from rat kidney," J. Biol. Chem. (1989) 264(10):5974-5980.

Ismail, N. et al., "Overproduction of TNF-alpha b CD8+ type 1 cells and down-regulation of IFN-γ production by CD4+ Th1 cells contribute to toxic shock-like syndrome in an animal model of fatal monocytotropic ehrlichiosis," J. Immunol. (2004) 172:1786-1800.

Karadimitris, A. et al., "Human CD1d-glycolipid tetramers generated by in vitro oxidative refolding chromatography," Proc. Natl. Acad. Sci. USA (2001) 98(6):3294-3298.

Kinjo, Y. et al., "Recognition of bacterial glycosphingolipids by natural killer T cells," Nature (2005) 434:520-525.

Kronenberg, M., "Toward an understanding of NKT cell biology: progress and paradoxes," Ann. Rev. Immunol (2005) 23:877-900.

Lee, P.T. et al., "Testing the NKT cell hypothesis on human IDDM pathogenesis," J. Clin. Invest. (2002) 110(6):793-800.

Mattner, J. et al., "Exogenous and endogenous glycolipid antigens activate NKT cells during microbial infections," Nature (2005) 434:525-529.

Matsuda, J.L. et al., "Tracking the response of natural killer T cells to a glycolipid antigen using CD1d tetramers," J. Exp. Med. (2000) 192(5):741-753.

Petrovsky, N. et al., "Vaccine adjuvants: current state and future trends," Immunol. Cell Biol. (2004) 82:488-496.

Rock, K.L. et al., "Natural endogenous adjuvants," Springer Semin. Immunopathol. (2005) 26:231-246.

Sidobre, S. et al., "CD1d tetramers: a powerful tool for the analysis of glycolipid reactive T cells," J. Immunol. Methods (2002) 268:107-121.

Van Kaer, L., "Alpha-galactosylceramide therapy for autoimmune diseases: prospects and obstacles," Nat. Rev. Immunol. (2005) 5:31-42.

Wu et al., "Bacterial glycolipids and analogs as antigen for CD1d-restricted NKT cells," PNAS (2005) 102(5):1351-1356.

Zajonc, D.M. et al., "Structure and function of a potent agonist for the semi-invariant natural killer T cell receptor," Nat. Immunol. (2005) 6:810-818.

Zhou, D. et al., "Lysosomal glycosphingolipid recognition by NKT cells," Science (2004) 306:1786-1789.

International Search Report and Written Opinion of International Searching Authority of PCT/US2007/072451 dated Nov. 27, 2007.

International Search Report and Written Opinion of International Searching Authority of PCT/US06/002781 dated Dec. 20, 2006.

Supplementary Search Report of the European Patent Office for Application No. 03816701.1 dated Sep. 17, 2007.

European Office Action for Application No. 03816701.1 dated Nov. 29, 2007.

Written Opinion of International Preliminary Examining Authority for International Application No. PCT/US03/08530 dated Jun. 30, 2005.

International Search Report of International Searching Authority for Application No. PCT/US03/08530 dated Aug. 3, 2004.

International Search Report and Written Opinion of International Searching Authority for International Application No. PCT/US07/66250 dated Oct. 15, 2007.

Liu, Y. et al., "A modified alpha-galactosyl ceramide for staining and stimulating natural killer T cells," J. Immun. Meth. (2006) 312(1-2):34-39.

Yu, K.O.A. et al., "Modulation of CD1d-restricted NKT cell responses by using N-acyl variants of alpha-galactosylceramides," Proc. Natl. Acad. Sci. USA (2005) 102(9):3383-3388.

* cited by examiner

Figure 1

NKT cell stimulatory activity of fluorophore-appended 6-amino-6-deoxygalactosylceramides 8, 10, 12. 1-♦ ; 8-● ; 10-▲ ; 12-■

Figure 2

NKT cell stimulatory activity of biotin-appended 6-amino-6-deoxygalactosylceramide 13. 1-♦ ; 13-■

6"-AMINO-6"-DEOXYGALACTOSYLCERAMIDES

CROSS REFERENCE TO RELATED APPLICATIONS

This application is the National Stage of International Application No. PCT/US2003/008530, filed on Mar. 20, 2003.

TECHNICAL FIELD

This invention relates to galactosylceramide compounds.

BACKGROUND

Peptide antigen presentation via major histacompatability complexes has long been recognized as a central element in adaptive immune responses. Recently, a parallel pathway that can elicit potent immune responses has begun to be elucidated. This pathway involves the presentation of glycolipids by CD1 proteins and is believed to be responsible for a portion of the innate immunity of mammals to bacteria The CD1 locus of mammals includes five distinct isotypes, CD1a, CD1b, CD1c, CD1d, and CD1e. These nonpolymorphic, membrane-bound proteins are characterized by their ability to present classes of glycolipids to T cells. The CD1d member of the gene family has been characterized by its ability to bind and present α-galactosylceramides to natural killer T cells (NKT cells).

Complex formation between glycolipid-loaded CD1d proteins and T cell receptors can subsequently lead to the stimulation of T cells. T cell stimulation initiates, inter alia, the cellular production of certain key immunoresponsive biochemicals.

SUMMARY

This invention relates to 6"-amino-6"-deoxygalactosylceramide compounds and their methods of use.

One aspect of this invention features compounds of Formula (I):

(I)

wherein, $R_1$ is:
(i) hydrogen; or
(ii) —$SO_2R_{10}$,
    wherein $R_{10}$ is:
    halo; hydroxy; $OR_{11}$; $OR_{12}$; amino; $NHR_{11}$; $N(R_{11})_2$; $NHR_{12}$; $N(R_{12})_2$; aralkylamino; or
    $C_1$-$C_{12}$ alkyl optionally substituted with halo, hydroxy, oxo, nitro, $OR_{11}$, $OR_{12}$, acyloxy, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, $C_3$-$C_{10}$ cycloalkyl containing is 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or heteroaryl containing 0-3 $R_{14}$; or
    $C_3$-$C_{10}$ cycloalkyl, $C_3$-$C_{10}$ heterocyclyl, $C_5$-$C_{10}$ cycloalkenyl, or $C_5$-$C_{10}$ heterocycloalkenyl optionally substituted with one or more halo, hydroxy, oxo, $OR_{11}$, $OR_{12}$, acyloxy, nitro, ammo, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl heteroaryl containing 0-3 $R_{14}$, or $C_6$-$C_{20}$ heteroaryl containing 0-3 $R_{14}$; or
    $C_2$-$C_6$ alkenyl, $C_2$-$C_6$ alkynyl, aryl, or heteroaryl optionally substituted with one or more halo, hydroxy, $OR_{11}$, $OR_{12}$, acyloxy, nitro, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or $C_6$-$C_{20}$ heteroaryl containing 0-3 $R_{14}$; or
(iii) —$C(O)R_{10}$, wherein $R_{10}$ is defined as above; or
(iv) —$C(R_{10})_2(R_{15})$, wherein $R_{10}$ is defined as above; $R_{15}$ is hydrogen, $R_{10}$, or $R_{15}$ and $R_2$ taken together forms a double bond between the carbon and nitrogen atoms to which they are attached; or
(v) $R_1$ and $R_2$ taken together forms a heterocyclyl of 3-10 ring atoms optionally substituted with $R_{10}$;

$R_2$ is hydrogen, or $R_2$ and $R_{15}$ taken together forms a double bond between the carbon and nitrogen atoms to which they are attached, or $R_2$ and $R_1$ taken together forms a heterocyclyl of 3-10 ring atoms optionally substituted with $R_{10}$;

$R_3$, $R_4$, $R_5$, $R_6$, and $R_7$ are each independently hydrogen, $C_1$-$C_6$ alkyl, $C_6$-$C_{12}$ aralkyl, or $C_1$-$C_6$ acyl;

$R_8$ is —$(CH_2)_xCH_3$;

$R_9$ is a linear or branched $C_3$-$C_{100}$ alkyl;

$R_{11}$ is $C_1$-$C_{20}$ alkyl optionally substituted with halo, hydroxy, alkoxy, amino, alkylamino, dialkylamino, sulfate, or phosphate;

$R_{12}$ is aryl optionally substituted with halo, haloalkyl, hydroxy, alkoxy, nitro, amino, alkylamino, dialkylamino, sulfate, or phosphate;

Each $R_{13}$ is independently halo, haloalkyl, hydroxy, alkoxy, oxo, amino, alkylamino, dialkylamino, sulfate, or phosphate;

Each $R_{14}$ is independently halo, haloalkyl, hydroxy, alkoxy, nitro, amino, alkylamino, dialkylamino, sulfate, or phosphate; and x is 1-100.

Referring to Formula (I) above, a subset of compounds described above are those in which x is 24 and $R_9$ is n-tetradecyl.

In some embodiments, $R_1$ is $SO_2R_{10}$ and $R_{10}$ can be aryl substituted with $N(R_{11})_2$, e.g.:

In other embodiments, $R_1$ is $C(O)R_{10}$ and $R_{10}$ can be $C_1$-$C_6$ alkyl substituted with halo, hydroxy, oxo, nitro, $OR_{11}$, $OR_{12}$, acyloxy, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or $C_6$-$C_{20}$ heteroaryl containing 0-3 $R_{14}$.

In certain embodiments, $R_{10}$ can be $C_1$-$C_6$ alkyl substituted with $NHSO_2R_{12}$, in which $R_{12}$ is e.g.:

In certain embodiments, $R_{10}$ can be alkyl substituted with $C(O)R_{12}$, in which e.g. $R_{12}$ is:

In certain embodiments, $R_{10}$ can be alkyl substituted with $C_5$-$C_{10}$ heterocyclyl containing 0-3 $R_{13}$ in which the heterocyclyl is e.g.:

In another aspect, this invention relates to a probe for observing glycolipid association with CD1d and NKT cell receptors during NKT cell stimulation having a compound of Formula (II):

wherein:

X is $-SO_2-$, $-C(O)-$, or absent;

Y is a linker group; and

Z is a reporter group.

In a further aspect, this invention relates to a method of quantifying glycolipid association with CD1d and NKT cell receptors during NKT cell stimulation including: (i) contacting a compound of Formula (II) with a CD1d protein; (ii) allowing the compound to associate with the CD1d protein; (iii) measuring fluorescence emitted by the compound during steps (i) and (ii) to provide one or more pre-NKT cell contact fluorescence measurements; (iv) contacting the compound and CD1d protein with an NKT cell line; (v) measuring fluorescence emitted by the compound during step (iv) to provide one or more NKT cell contact fluorescence measurements.

Embodiments can include one or more of the following features.

Step (v) can be repeated over time.

The method can further include the step of comparing the fluorescence measurements in steps (iii) and (v).

In one aspect, this invention features a method of stimulating NKT cells, which includes contacting an NKT cell with a compound of Formula (I) and a CD1 protein.

The protein can be a CD1d protein.

In another aspect, this invention features a method of stimulating the immune system of a subject (e.g., mammal, human, dog, horse, cat) in need of such stimulation, the method includes administering a compound of Formula (I) to the subject.

In a further aspect, this invention features a method of treating an autoimmune disease in a subject (e.g., mammal, human, dog, horse, cat) in need of such treatment, the method includes administering an effective amount of a compound of Formula (I).

The subject can be a mammal, preferably a human. Identifying a subject in need of such treatment can be in the judgment of a subject or a health care professional and can be subjective (e.g., opinion) or objective (e.g., measurable by a test or diagnostic method).

In one aspect, this invention relates to a method of making a compound described herein. In some embodiments, the method can be a method of making a compound of Formula (I) including: (i) converting a compound of Formula (III) to a compound of Formula (IV):

(III)

(IV)

and (ii) contacting a compound of Formula (IV) with $R_1$-LG to afford a compound of Formula (I), wherein:

$R_1$ is:
(i) —$SO_2R_{10}$,
wherein $R_{10}$ is:
halo; hydroxy; $OR_{11}$; $OR_{12}$; amino; $NHR_{11}$; $N(R_{11})_2$; $NHR_{12}$; $N(R_{12})_2$; aralkylamino; or $C_1$-$C_{12}$ alkyl optionally substituted with halo, hydroxy, oxo, nitro, $OR_{11}$, $OR_{12}$, acyloxy, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or $C_6$-$C_{20}$ heteroaryl containing 0-3 $R_{14}$; or $C_3$-$C_{10}$ cycloalkyl, $C_3$-$C_{10}$ heterocyclyl, $C_5$-$C_{10}$ cycloalkenyl, or $C_5$-$C_{10}$ heterocycloalkenyl optionally substituted with one or more halo, hydroxy, oxo, $OR_{11}$, $OR_{12}$, acyloxy, nitro, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or $C_6$-$C_{20}$ heteroaryl containing 0-3 $R_{14}$; or $C_2$-$C_6$ alkenyl, $C_2$-$C_6$ alkynyl, aryl, or heteroaryl optionally substituted with one or more halo, hydroxy, $OR_{11}$, $OR_{12}$, acyloxy, nitro, amino, $NHR_{11}$, $N(R_{11})_2$, $NHR_{12}$, $N(R_{12})_2$, aralkylamino, mercapto, thioalkoxy, $S(O)R_{11}$, $S(O)R_{12}$, $SO_2R_{11}$, $SO_2R_{12}$, $NHSO_2R_{11}$, $NHSO_2R_{12}$, sulfate, phosphate, cyano, carboxyl, $C(O)R_{11}$, $C(O)R_{12}$, $C(O)OR_{11}$, $C(O)NH_2$, $C(O)NHR_{11}$, $C(O)N(R_{11})_2$, alkyl, haloalkyl, $C_3$-$C_{10}$ cycloalkyl containing 0-3 $R_{13}$, $C_3$-$C_{10}$ heterocyclyl containing 0-3 $R_{13}$, $C_2$-$C_6$ alkenyl, $C_2$-$C_6$ alkynyl, $C_5$-$C_{10}$ cycloalkenyl, $C_5$-$C_{10}$ heterocycloalkenyl, $C_6$-$C_{20}$ aryl containing 0-3 $R_{14}$, or $C_6$-$C_{20}$ heteroaryl containing 0-3 $R_{14}$; or (ii)-$C(O)R_{10}$, wherein $R_{10}$ is defined as above; or
(iii)-$C(R_{10})_2(R_{15})$, wherein $R_{10}$ is defined as above; $R_{15}$ is hydrogen, $R_{10}$, or $R_{15}$ and $R_2$ taken together forms a double bond between the carbon and nitrogen atoms to which they are attached; or $R_3$, $R_4$, $R_5$, $R_6$ and $R_7$ are each independently hydrogen, $C_1$-$C_6$ alkyl, $C_6$-$C_{12}$ aralkyl, or $C_1$-$C_6$ acyl;

R is —$(CH_2)_xCH_3$;

$R_9$ is a linear or branched $C_3$-$C_{100}$ alkyl;

$R_{11}$ is $C_1$-$C_{20}$ alkyl optionally substituted with halo, hydroxy, alkoxy, amino, alkylamino, dialkylamino, sulfate, or phosphate;

$R_{12}$ is aryl optionally substituted with halo, haloalkyl, hydroxy, alkoxy, nitro, amino, alkylamino, dialkylamino, sulfate, or phosphate;

Each $R_{13}$ is independently halo, haloalkyl, hydroxy, alkoxy, oxo, amino, alkylamino, dialkylamino, sulfate, or phosphate;

Each $R_{14}$ is independently halo, haloalkyl, hydroxy, alkoxy, nitro, amino, alkylamino, dialkylamino, sulfate, or phosphate;

x is 1-100;

LG is halo, —$OSO_2R_{16}$, B(OH)$_2$, or

; and $R_{16}$ is alkyl, haloalkyl or aryl optionally substituted with alkyl, halo or nitro.

In another aspect, this invention features a pharmaceutical composition including a compound of Formula (I) and a pharmaceutically acceptable carrier.

Also within the scope of this invention is a composition containing one or more of the compounds described herein for use in treating cancer or autoimmune disorders, diseases, or disease symptoms, including any of those delineated herein, and the use of such a composition for the manufacture of a medicament for the just-mentioned use.

Also within the scope of this invention is a packaged product. The packaged product includes a container, one of the aforementioned compounds in the container, and a legend (e.g., a label or insert) associated with the container and indicating administration of the compound for treating cancer or autoimmune disorders, diseases, or disease symptoms, including any of those delineated herein.

Embodiments of the invention may have one or more of the following advantages. For example, the replacement of the parent sugar's $C_6"$-hydroxyl by the more reactive amino group allows for the efficient synthesis of a more expansive range of $C_6"$-amino-$C_6"$-deoxygalactosylceramides. Further, having the derivitization handle situated at $C_6"$ allows α-galactosylceramides to be modified without significantly altering their binding to the proteins and receptors involved in T cell stimulation because the $C_6"$-amino substituents are sufficiently distanced from the lipid portion of the molecule, which is known to engage in relatively strong interactions with the deep hydrophobic pockets of the CD1d proteins.

The details of one or more embodiments of the invention are set forth in the accompanying drawings and the description below. Other features, objects, and advantages of the invention will be apparent from the description and drawings, and from the claims.

DETAILED DESCRIPTION

As used herein, the term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$–$C_{12}$ alkyl indicates that the group may have from 1 to 12 (inclusive) carbon atoms in it. The terms "arylalkyl" or "aralkyl" refer to an alkyl moiety in which an alkyl hydrogen atom is replaced by an aryl group. Examples of "arylalkyl" or "aralkyl" include benzyl and 9-fluorenyl groups.

The terms "alkylamino" and "dialkylamino" refer to —NH(alkyl) and —NH(alkyl)$_2$ radicals respectively. The term "aralkylamino" refers to a —NH(aralkyl) radical. The term "alkoxy" refers to an —O-alkyl radical. The term "mercapto" refers to an SH radical. The term "thioalkoxy" refers to an —S-alkyl radical.

The term "aryl" refers to an aromatic monocyclic, bicyclic, or tricyclic hydrocarbon ring system, wherein any ring atom capable of substitution can be substituted by a substituent. Examples of aryl moieties include, but are not limited to, phenyl, naphthyl, and anthracenyl.

The term "cycloalkyl" as employed herein includes saturated cyclic, bicyclic, tricyclic, or polycyclic hydrocarbon groups having 3 to 12 carbons, wherein any ring atom capable of substitution can be substituted by a substituent. Examples of cycloalkyl moieties include, but are not limited to, cyclohexyl and adamantyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom capable of substitution can be substituted by a substituent. Examples of cycloalkyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom capable of substitution can be substituted by a substituent.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound that confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, alternatively from about 1 to about 50 mg/Kg. Effective doses will also vary depending on route of administration, as well as the possibility of co-usage with other agents.

The term "mammal" includes organisms, which include mice, rats, cows, sheep, pigs, goats, and horses, monkeys, dogs, cats, and preferably humans.

Structure of 6"-amino-6"-deoxygalactosylceramide Compounds

In general, the 6"-amino-6"-deoxygalactosylceramide compounds include a "glyco" portion and a "lipid" portion as indicated in Formula (V). The two portions are appended to one another via an α-glycosidic bond between the anomeric carbon, $C_a$, of the "glyco" portion and the oxygen (bolded) bound to $C_1$ of the "lipid" portion.

"glyco" portion

"lipid" portion (V)

The lipid portion is a chain of carbon atoms having functionalized and unfuctionalized segments. The functionalized segment includes carbons $C_1$-$C_4$. The functionalized segment terminus $C_1$ is the carbon through which the lipid portion is appended to the glyco portion of the molecule. The remaining members of this segment, $C_2$, $C_3$, and $C_4$, each contain a heteroatom substituent. The $C_2$ nitrogen is acylated with C(O)$R_8$, in which $R_8$ is a hydrocarbon chain represented by the formula $(CH_2)_xCH_3$. The hydrocarbon chain $R_8$ can have 1 to 100 methylene ($CH_2$) groups (e.g., 1 to 75 $CH_2$ groups, 1 to 50 $CH_2$ groups, 1 to 25 $CH_2$ groups, 1 to 20 $CH_2$ groups, 1 to 15 $CH_2$ groups, 1 to 10 $CH_2$ groups, or 1 to 5 $CH_2$ groups). In certain embodiments, $R_8$ contains 24 $CH_2$ groups. The oxygens on $C_3$, and $C_4$, may be substituted with hydrogen, alkyl, aralkyl, trisubstituted silyl, or acyl groups. In some embodiments, $R_5$ and $R_6$ are hydrogen, and in other embodiments, they are tert-butyldimethylsilyl (TBS).

The unfunctionalized segment is represented by $R_9$, which can include any branched or unbranched alkyl group containing 3-100 carbons atoms (e.g, 3-75 carbons atoms, 3-50 carbons atoms, 3-25 carbons atoms, 3-20 carbons atoms, 3-15 carbons atoms, or 3-10 carbons atoms). In certain embodiments, $R_9$ contains an unbranched alkyl group composed of 14 carbon atoms.

The glyco portion is a derivative of α-D- galactose. Each of $R_3$, $R_4$, and $R_5$ may be hydrogen, alkyl, aralkyl or acyl groups. When $R_3$-$R_5$ are substituted with a group other than hydrogen, the group is preferably one that is readily removed using carbohydrate deprotection chemistries that are well known in the art. In certain embodiments, these groups include methyl, benzyl or acetyl.

The $C_6''$-hydroxyl group of the parent sugar is replaced by a substituted ($R_1$ and/or $R_2$ are substituents other than hydrogen) or unsubstituted ($R_1$ and $R_2$ are both hydrogen) amino group.

In certain embodiments, the $C_6''$-amino group is monosubstituted ($R_1$=substitutent and $R_2$=H). For example, the $C_6''$-nitrogen can form part of a sulfonamide ($R_1$=—$SO_2R$) or amide ($R_1$=C(O)R group. R may include e.g., substituted or unsubstituted alkyl, cycloalkyl, aryl, heteroaryl, etc. These groups can be formed upon the reaction of the unsubstituted amino group with e.g., the corresponding sulfonyl halide or activated acyl derivative. Alternatively, the nitrogen may form part of a secondary alkyl-alkyl or alkyl-aryl amino group (e.g., $R_1$=substituted or unsubstituted alkyl or aryl). Introduction of an alkyl group at $R_1$ can be carried out e.g., by first exposing the unsubstituted amino group to a carbonyl compound and then performing a reductive alkylation on the resulting, intermediary aldimine or ketenimine. Introduction of an aryl group at $R_1$ can be accomplished e.g., by transition metal mediated coupling between the unsubstituted amino group and an aryl halide or triflate.

In other embodiments, the $C_6''$-amino group is disubstituted ($R_1$ and $R_2$=substituent). In some embodiments, $R_1$ and $R_2$ may form a cyclic structure in which one or more of the ring atoms may be a heteroatom (e.g., N, O, or S). Further, any one of the ring atoms may be substituted with e.g., halo, hydroxy, alkyl, haloalkyl, aryl, herteroaryl, etc.

In some embodiments, the $C_6''$-nitrogen can form part of an imino group, i.e., C=N. The imino group can be an aldimine, which may be obtained in a condensation reaction between the $C_6''$-amino group and a substituted or unsubstituted alkyl or aryl aldehyde. Similarly, the imino group can be a ketenimine, which may be obtained in a condensation reaction between the $C_6$-amino group and a substituted or unsubstituted dialkyl ketone, a diarylketone, aryl-alkyl ketone, etc.

In certain embodiments, it can be advantageous for a reporter group to be linked either directly or indirectly to the C6''-amino group. While not wishing to be bound by theory, it believed that labelling galactosylceramides with fluorophores or other small molecules (e.g., biotin) would allow observation of the compounds at low concentrations and/or provide a means of quantifying association with CD1d and NKT cell receptors. Thus compounds containing reporter groups could be useful as probes for determining e.g., specific structural requirements for glycolipid binding by CD1d and T cell receptors.

In some embodiments, probes are compounds in which the reporter group may be directly attached to the $C_6''$-amino group in either a covalent or noncovalent manner. In other embodiments, the reporter group may be indirectly attached to the $C_6$-amino group via covalent or noncovalent linkages. For example, when the reporter group is indirectly attached, the $C_6''$-amino group can be attached to a moiety —X—Y-Z, wherein X is —SO2—, —C(O)—, or absent; Y is a linker group, and Z is a reporter group.

The linker group Y can be any carbon-containing chain or ring. For example, the linker can be —$(CH_2)_t$—, in which the chain optionally contains one or more terminal heteroatoms (e.g., N, O, S), and/or one or more heteroatoms, rings, double bonds, triple bonds that are inserted into the chain. The value of "t" can be 1-100. The linker may also be one ring, or a series of two or more rings.

The reporter groups may be selected as desired. Selection of the reporter groups is within skill of the art. Examples of reporter groups include labelling reagents, e.g., radiolabelled moieties, functional small molecules, e.g., biotin, or fluorophores e.g., acridines, Cy5.5™, Dabcyl, Dansyl, Fluorescien, Oregon Green 488, Prodan, Tamra, etc. Representative reporter groups may be selected and obtained from e.g., Molecular Probes, Inc. (www.molecularprobes.com).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Synthesis of 6"-amino-6"-deoxygalactosylceramide compounds

The synthesis of 6"-amino-6"-deoxygalactosylceramides may be carried out using conventional methods including those described herein for exemplary compound 1 ($R_3$-$R_7$=H; R=$(CH_2)_{24}CH_3$; and $R_9$=$C_{14}H_{29}$). In general, compound 1 may be obtained from the reaction between compound 2 and a desired electrophile, e.g., $R_1$-leaving group, as shown below.

1

⇓

2

The synthesis of compound 2 can be carried out as follows. The amine functionality was incorporated early onto the carbohydrate as the azide using the procedure of Corey et al., *J. Am. Chem. Soc.* 1984, 106, 3682. (3, Scheme 1). Following the procedure of Singh, P. P., et al., *Carbohyd. Res.* 1970, 12, 261, the acetonides were hydrolyzed with concomitant methylgalactoside formation and benzyl ethers at C2, C3 and C4 were formed giving 4. The methoxy group was then replaced by an acetoxy group, followed by conversion to the anomeric fluoride (5) according to the methods of Davis, N. J., et al., *J. Chem. Soc. Perkin Trans.* 1 1994, 359 and Hayashi, M., et al., *Chem. Lett.* 1984, 1747 respectively. Glycosyl bond formation with compound 6 gave 7 via Hashimoto, et al., *Tetrahedron Lett.* 1984, 25, 1379. Compound 6, (2S,3S,4R)-3,4bis-t-butyldimethylsisyloxy-2-hexaosanoylamino-4-octadecanol, was prepared by coupling of phytosphingosine (Avanti Polar Lipids) with hexacosanoic acid using 2-dimethylaminoisopropyl chloride hydrochloride (DIC) and 1-hydroxybenzotriazole (HOBT), followed by the protection/deprotection scheme reported by Takikawa, et al., *Tetrahedron* 1998, 54, 3141. The silyl protecting groups were removed (Takikawa, et al.) followed by reduction of the azide (Vaultier, M. et al., *Tetrahedron Lett.* 1983, 24, 763) and removal of the benzyl groups giving 2 (Sakai, T. et al., *J. Med. Chem.* 1998, 41, 650).

Reagents (yields in parentheses): a) AcCl, MeOH (86% yield). b) BnBr, 18-crown-6, NaH, THF (95% yield). c) AcOH, $H_2SO_4$ (84% yield). d) HF.pyridine, pyridine (78% yield). e) MS 4 Å, $AgClO_4$, $SnCl_2$, THF (44% yield). f) TBAF, THF (81% yield). g) $PPh_3/H_2O$, THF (quant. yield). h) $NH_3$/Na, −78° C. (53% yield).

Reaction of 2 with acid chlorides and N-hydroxysuccinimidyl (NHS) esters can provide reasonable yields of the corresponding amides. For example, compounds 8 and 10 were prepared from 2 and dansyl chloride and 9 respectively (Scheme 2). The latter compound is a dansyl amide tethered to an N-hydroxysuccinimidyl ester (Wang, F.; Schwabacher, A. W. *J. Org. Chem.* 1999, 64, 8922). NHS ester 11 can be prepared from 4-(6-methoxy-[2]naphthyl)-4-oxo-butyric acid (Khan, M. et al., *Indian J. Chem. Sect. B* 2000, 39, 614) by nucleophilic displacement of the methoxy group with lithium dimethylamide (Weber, G., et al., *Biochemistry* 1979, 18, 3075) followed by reaction with dicyclohexylcarbodiimide (DCC) and N-hydroxysuccinimide. Reaction of NHS ester 11 with 2 gave 12 in 46% yield. Similarly, reaction of 2 with the N-hydroxysuccinimidyl ester of biotin gave 13 in 52% yield (Scheme 3). Glycosylceramides can exhibit relatively limited solubility in many organic solvents, and this relatively high insolubility may result in loss of yield, e.g., during purification.

The synthesized 6"-amino-6"-deoxygalactosylceramide compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The 6"-amino-6"-deoxygalactosylceramide compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The 6"-amino-6"-deoxygalactosylceramide compounds of this invention include the compounds themselves, as well as their salts and their prodrugs, if applicable. A salt, for example, can be formed between an anion and a positively charged substituent (e.g., amino) on a 6"-amino-6"-deoxygalactosylceramide compound. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a 6"-amino-6"-deoxygalactosylceramide compound. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active 6"-amino-6"-deoxygalactosylceramide compounds.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Methods of Using 6"-amino-6"-deoxygalactosylceramide compounds

The effect of a particular $C_6$"-substitution on a 6"-amino-6"-deoxygalactosylceramide compound's ability to stimulate NKT cells can be evaluated e.g., by measuring interleukin (IL)-2 production using an immobilized CD1d assay (Benlagha, K.; Weiss, A.; Beavis, A.; Teyton, L.; Bendalac, A. *J. Exp. Med.* 2000, 191, 1895). The assay includes loading soluble, biotinylated CD1d onto precoated avidin plates, pulsing the plates with incrementally varied concentrations of glycolipids, washing the plates, treating the plates with a CD1d-restricted Vα24 NKT cell hybridoma, and measuring IL-2 release using ELISA (enzyme-linked immunosorbent assay).

Each compound's NKT cell stimulating ability is compared against that of the reference compound, KRN7000, 14 (Morita, M., et al., *J. Med. Chem.* 1995, 38, 2176.).

Figure 1:
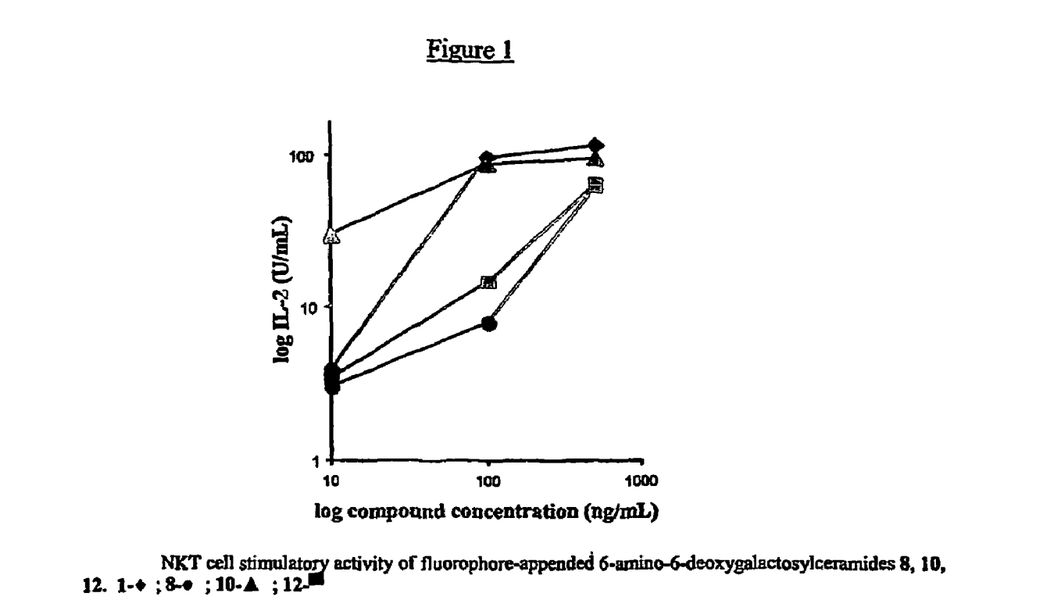
FIG. 1 shows NKT cell stimulatory activity of fluorophore-appended $C_6''$-amino-$C_6''$-deoxygalactosylceramides 8, 10, 12.
Figure 2:
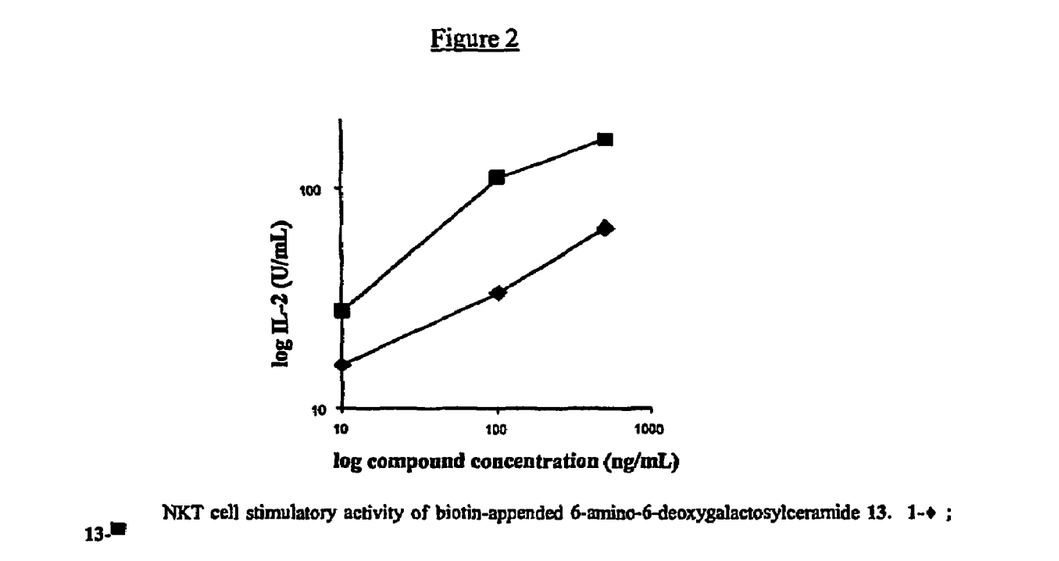
FIG. 2 shows NKT cell stimulatory activity of biotin-appended $C_6''$-amino-$C_6''$-deoxygalactosylceramide 13.

Compounds 8, 10, 12 and 13 were determined to possess relatively high NKT cell stimulating abilities according to the above assay. The results in FIGS. 1 and 2 indicate that there is a dose-dependent response to the glycolipids (i.e., cytokine release) and that this response is comparable to that of the reference compound. Although 8 and 12 appear slightly less efficient in the results from the experiment shown in FIG. 1, no significant differences among the compounds were found in repeated experiments (at least three experiments for each compound). In a separate series of experiments (e.g., FIG. 2), compound 13 was slightly, but reproducibly more efficient in stimulating NKT cells than 1. Similar results were observed using CD1d transfected rat basophilic leukemia cells for antigen presentation to NKT cell hybridomas.

The attachment of a dansyl group directly at $C_6$" (as in 8) or through a five carbon tether (as in 10) did not cause a significant loss of stimulating properties. Similarly, alteration of the appended group (i.e., dansyl vs. prodan vs. biotin) did not greatly affect the abilities of these glycolipids to stimulate NKT cells.

Binding of the glycolipids with CD1d and NKT cell receptors can be visualized by fluorescence modulation studies, fluorescence and surface plasmon resonance studies, which employ 6"-amino-6"-deoxygalactosylceramide probe compounds that contain one or more reporter groups attached directly or indirectly to the 6"-amino group (e.g., probe compounds described herein). In certain embodiments, probes that contain fluorophores as the reporting group can be used to quantify the association between the glycolipids and CD1d and the NKT cell receptors during NKT cell stimulation. The selection of experimental protocols to observe association are within the art and are described in Kasten, F. H., "Introduction to Fluorescent Probes: Properties, History and Applications" in *Fluorescent and Luminescent Probes for Biological Activit*, W. T. Mason, Ed., Academic Press (1993) pp. 12-33 and Lakowicz, J. R., Ed., *Topics in Fluorescence Spectroscopy: Probe Design and Chemical Sensing* (*Volume* 4), Plenum Publishing (1994).

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions delineated herein include the compounds of the formulae delineated herein, as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds of the invention can be used in the treatment of cancer. The cancer can be, but is not limited to: a human leukemia, sarcoma, osteosarcoma, lymphoma, melanoma, ovarian, skin, testicular, gastric, pancreatic, renal, breast, prostate colorectal, head and neck, brain, esophageal, bladder, adrenal cortical, lung, bronchus, endometrial, cervical or hepatic cancer, or cancer of unknown primary site.

The compounds of the invention can also be used in the treatment of an autoimmune diseases. The autoimmune disease can be, but is not limited to: (1) a rheumatic disease such as rheumatoid arthritis, systemic lupus erythematosus, Sjögren's syndrome, scleroderma, mixed connective tissue disease, dermatomyositis, polymyositis, Reiter's syndrome or Behcet's disease (2) type I or type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus foliaceus, Senear-Usher syndrome, or Brazilian phemphigus, (6) diseases of the skin such as psoriasis or neurodermitis, and (7) inflammatory bowel disease (e.g., ulcerative colitis or Crohn's Disease).

The invention will be further described in the following examples. It should be understood that these examples are for illustrative purposes only and are not to be construed as limiting this invention in any manner.

EXAMPLE 1

Preparation of 6-azido-2,3,4-tetra-O-benzyl-6-deoxymethylgalactopyranoside (4)

Compound 3 (1.86 g, 6.52 mmol) was dissolved in MeOH (20 mL), cooled to 0° C., and acetyl chloride (4.35 mL) was added. The mixture was allowed warm to room temperature and stirred for 12 h. The solvent was removed in vacuo, and the residue was chromatographed ($SiO_2$, 10% MeOH in $CH_2Cl_2$) to afford 6-azido-6-deoxymethylgalactopyranoside (mixture of anomers) as a white solid (1.23 g, 86% yield). $^1$H NMR (10% $CD_3OD$ in $CDCl_3$) δ 4.79 (d, J=2.5 Hz, 1H), 4.46 (br, 1H), 3.92 (dd, J=8.5, 4.0 Hz, 1H), 3.84-3.75 (m, 3H), 3.63 (dd, J=12.5, 8.5 Hz, 1H), 3.46 (s, 3H), 3.31 (dd, J=13.0, 4.5 Hz, 1H); $^{13}$C NMR (10% $CD_3OD$ in $CDCl_3$) δ 99.80, 69.84, 69.66, 69.54, 68.55, 55.08, 51.21; HRFAB-MS (thioglycerol+$H^+$ matrix) m/e ([M+H]$^+$) 220.0951(3.1%), calcd 220.0933.

To a mixture of 6-azido-6-deoxymethylgalactopyranoside (482 mg, 2.2 mmol) in THF (30 mL) was added benzyl bromide (1.57 mL, 13.2 mmol), $K_2CO_3$ (2.4 g, 17.6 mmol) and 18-crown-6 (120 mg). The suspension was stirred for 15 min, and NaH (0.396 g, 60% in mineral oil, 16.5 mmol) was added. After 12 h, brine (30 mL) was added and the product was extracted with 10% EtOAc in hexane (3×20 mL). The combined extracts were dried over $Na_2SO_4$ and concentrated in vacuo. The desired product 4 (1.02 g, 95% yield) was obtained as a clear oil after chromatography ($SiO_2$, EtOAc:

hexanes 1:2). NMR ($^1$H, CDCl$_3$) δ 7.40-7.25 (m, 15H), 5.02-4.62 (m, 7H), 4.14-3.76 (m, 4H), 3.57-3.48 (m, 1H), 3.39 (s, 3H), 2.94 (dd, J=12.4, 4.4 Hz, 1H); NMR ($^{13}$C, CDCl$_3$) δ 138.65, 138.58, 138.34, 128.68, 128.61, 128.32, 128.12, 128.01, 127.87, 127.78, 99.01, 79.16, 76.48, 75.45, 74.81, 73.89, 69.98, 55.71, 51.64; HRFAB-MS (thioglycerol+H$^+$ matrix) m/e ([M+H]$^+$) 490.2347(3.6%), calcd 490.2342.

EXAMPLE 2

Preparation of 6-azido-2,3,4-tetra-O-benzyl-6-deoxy-α-galactosyl fluoride (5)

Acetic anhydride (0.45 mL) was added to a solution of 4 (398 mg, 0.81 mmol) in acetic acid (0.33 mL). The mixture was cooled to 0° C., and conccentrated H$_2$SO$_4$ (6.8 μl) was added. The mixture was stirred at 0° C. for 8 h, and H$_2$O (5 mL) was is added. The product was extracted with CH$_2$Cl$_2$ (3×5 mL), and the combined extracts were dried over Na$_2$SO$_4$ and concentrated in vacuo. After chromatography (SiO$_2$, EtOAc:hexanes 1:2), 6-azido-2,3,4-tetra-O-benzyl-6-deoxy-α-galactosyl 1-acetate (354 mg, 84% yield) was obtained as a clear oil. NMR ($^1$H, CDCl$_3$) δ 7.39-7.28 (m, 15H), 6.38 (d, J=3.5 Hz, 1H), 5.02-4.58 (m, 6H), 4.17 (dd, J=11.0, 4.0 Hz, 1H), 3.91-3.88 (m, 3H), 3.47 (dd, J=12.5, 7.0 Hz, 1H), 3.15 (dd, J=12.5, 7.0 Hz, 1H), 2.12 (s, 3H); NMR ($^{13}$C, CDCl$_3$) δ 169.55, 138.59, 138.13, 138.00, 128.68, 128.62, 128.57, 128.56, 128.53, 128.51, 128.18, 128.13, 128.10, 128.03, 127.98, 127.85, 127.79, 127.60, 90.65, 78.67, 75.45, 75.31, 74.95, 74.69, 74.60, 74.42, 73.57, 73.53, 71.89, 50.85, 21.28; HRFAB-MS (thioglycerol+Na$^+$ matrix) m/e ([M+Na]$^+$) 540.2112(100%), calcd 540.2111.

Anhydrous pyridine (0.6 mL) and 70% hydrogen fluoride-pyridine (1.5 mL) were placed in a 50-ml polyethylene vessel. To this mixture cooled to −20° C. was added a solution of 6-azido-2,3,4-tetra-O-benzyl-6-deoxy-α-galactosyl 1-acetate (401 mg, 0.77 mmol) in toluene (0.3 mL). The mixture was allowed to warm to 0° C. and stir for 6 h then poured into a mixture of ether (10 mL) and saturated aqueous potassium fluoride (30 mL). The product was extracted with a 3:1 ether-hexane solution (2×50 mL), and the combined extracts were washed with saturated aqueous potassium fluoride (30 mL) and brine (30 mL). The organics were dried over Na$_2$SO$_4$ and the solvent was removed in vacuo. The residue was purified chromatographically (SiO$_2$, EtOAc:hexanes 1:2) to give 6-azido-2,3,4-tetra-O-benzyl-6-deoxy-α-galactosyl fluoride as a clear oil (230 mg, 78% yield). NMR ($^1$H, CDCl$_3$) δ 7.40-7.25 (m, 15H), 5.63 (dd, J=54.0, 2.5 Hz, 1H), 5.00 (d, J=11.5 Hz, 1H), 4.88-4.72 (m, 4H), 4.61 (d, J=11.0 Hz, 1H), 4.01-3.88 (m, 4H), 3.51 (dd, J=12.5, 7.5 Hz, 1H), 3.13 (dd, J=12.0, 6.0 Hz, 1H); NMR ($^{13}$C, CDCl$_3$) δ 138.38, 138.09, 138.07, 128.74, 128.71, 128.66, 128.56, 128.23, 128.20, 128.16, 128.04, 127.80, 107.12, 105.32, 78.45, 75.85, 75.67, 74.99, 74.48, 73.99, 73.67, 72.14, 72.11, 50.96; HRFAB-MS (thioglycerol+Na$^+$ matrix) m/e ([M+Na]$^+$) 500.1956(100%), calcd 500.1962.

EXAMPLE 3

Preparation of Compound 7

To a solution of (2S, 3S, 4R)-3,4,-bis-t-butyldimethylsilyloxy-2-hexacosanoylamino-4-octadecanol (6) (266 mg, 0.28 mmol) in THF (10 mL), SnCl$_2$ (163.7 mg, 0.86 mmol), AgClO$_4$ (179 mg, 0.86 mmol) and powdered 4 Å molecular sieves (1.34 g) were added. A solution of 5 (214 mg, 0.45 mmol) in THF (2 mL) was then added at −10° C. The reaction mixture was allowed to warm gradually to room temperature with stirring over the course of 2 h. The mixture was filtered through Celite, and the filter cake was washed with Et$_2$O. The combined filtrate was concentrated under reduced pressure. The residue was purified chromatographically (SiO$_2$, EtOAc: hexanes 1:2) to give compound 7 (175 mg, 44% yield) as a clear oil. NMR ($^1$H, CDCl$_3$) δ 7.40-7.31 (m, 15H), 5.92 (d, J=8.0 Hz, 1H), 5.02 (d, J=11.0 Hz, 1H), 4.85-4.59 (m, 6H), 4.21 (m, 1H), 4.06-3.99 (m, 2H), 3.91 (dd, J=13.0, 3.0 Hz, 1H), 3.86-3.83 (m, 3H), 3.79 (m, 1H), 3.50 (dd, J=12.0, 7.5 Hz, 1H), 3.17 (dd, J=12.0, 7.5 Hz, 1H), 2.03 (t, J=7.5 Hz, 2H), 1.58-1.24 (m, 73H), 0.92 (s, 9H), 0.91 (s, 9H), 0.89 (m, 6H), 0.09 (s, 3H), 0.08 (s, 3H), 0.06 (s, 3H), 0.05 (s, 3H); NMR ($^{13}$C, CDCl$_3$) δ 173.24, 138.69, 138.61, 138.35, 128.64, 128.58, 128.57, 128.06, 128.03, 127.94, 127.85, 127.64, 100.18, 79.16, 76.59, 76.20, 75.99, 75.04, 74.87, 73.71, 73.49, 70.11, 69.56, 51.78, 51.38, 37.05, 33.59, 32.14, 32.13, 30.10, 29.93, 29.91, 29.89, 29.87, 29.81, 29.77, 29.68, 29.66, 29.58, 26.31, 26.24, 25.86, 22.90, 18.52, 18.37, 14.34, −3.471, −3.756, −4.442, −4.705; HRFAB-MS (thioglycerol+H$^+$ matrix) m/e ([M+H]$^+$) 1382.0592(81.3%), calcd 1382.0601.

EXAMPLE 4

Preparation of Compound 2

To a solution of 7 (175 mg, 0.12 mmol) in THF (4 mL), TBAF (1.0 M in THF, 0.5 mL, 0.5 mmol) was added dropwise at room temperature. After stirring for 1.5 h, the mixture was diluted with water and extracted with Et$_2$O. The extract was washed with water and brine, dried (MgSO$_4$), and concentrated under reduced pressure. The residue was purified by column chromatography (SiO$_2$, EtOAc:hexanes 1:2) to give the corresponding diol (118 mg, 81% yield) as a clear glass. NMR ($^1$H, CDCl$_3$) δ 7.39-7.25 (m, 15H), 6.25 (d, J=8.0 Hz, 1H), 4.99 (d, J=11.0 Hz, 1H), 4.88-4.57 (m, 6H), 4.27 (m, 1H), 4.05 (dd, J=9.5; 3.0 Hz, 1H), 3.93 (dd, J=10.0, 3.0 Hz, 1H), 3.87-3.80 (m, 2H), 3.72 (m, 1H), 3.51-3.45 (m, 3H), 3.03 (dd, J=13.0, 6.0 Hz, 1H), 2.25 (d, J=5.5 Hz, 1H), 2.15 (t, J=7.0 Hz, 2H), 2.13-1.25 (m, 76H), 0.88 (t, J=7.5 Hz, 6H); NMR ($^{13}$C, CDCl$_3$)δ 173.07, 138.30, 138.12, 137.84, 128.75, 128.74, 128.64, 128.58, 128.32, 128.29, 128.20, 128.02, 127.72, 99.08, 79.38, 76.41, 75.93, 74.84, 74.60, 74.49, 73.54, 73.27, 70.42, 69.99, 51.22, 49.28, 37.03, 33.58, 32.13, 29.94, 29.91, 29.88, 29.75, 29.63, 29.57, 29.52, 26.12, 25.98, 22.90, 14.33; HRFAB-MS (thioglycerol+H$^+$ matrix) m/e ([M+H]$^+$) 1151.9072(89.4%), calcd 1151.9079.

To a solution of the diol (118 mg, 0.1 mmol) in THF/H$_2$O (1.5 mL/0.3 mL) was added triphenylphosphine (40.3 mg). The reaction mixture was stirred at room temperature for 12 h. The resulting amine (114 mg, 99% yield) was obtained as a clear glass after chromatography (SiO$_2$, CHCl$_3$:MeOH:NH$_3$—H$_2$O 1:0.4:0.02). NMR ($^1$H, CDCl$_3$) δ7.59-7.18 (m, 15H), 6.49 (d, J=8.5 Hz, 1H), 4.87 (d, J=11.5 Hz, 1H), 4.78-4.52 (m, 6H), 4.18 (m, 1H), 3.97 (dd, J=10.0, 3.5 Hz, 1H), 3.81 (dd, J=10.0, 4.5 Hz, 1H), 3.77 (dd, J=10.0, 2.5 Hz, 1H), 3.72 (m, 2H), 3.67 (dd, J=10.0, 4.0 Hz, 1H), 3.52 (dd, J=8.0, 5.0 Hz, 1H), 3.41 (m, 2H), 2.82 (dd, J=13.0, 8.0 Hz, 1H), 2.42 (dd, J=13.0, 5.0 Hz, 1H), 2.37 (m, 1H), 2.04 (t, J=8.0 Hz, 2H), 1.49-0.82 (m, 74H), 0.79 (t, J=7.0 Hz, 6H);); NMR ($^{13}$C, CDCl$_3$) δ 173.54, 138.60, 138.33, 138.12, 132.96, 132.31, 132.23, 132.19, 132.17, 132.14, 128.76, 128.74, 128.66, 128.59, 128.24, 128.11, 128.09, 127.86, 127.69, 98.86, 79.81, 76.50, 76.35, 74.79, 74.62, 74.08, 73.37, 73.03, 72.58, 68.51, 53.93, 50.42, 42.43, 36.97, 33.88, 32.11, 29.96, 29.90, 29.84, 29.74, 29.61, 29.55, 29.52, 26.16, 25.97, 25.86, 22.88, 20.92, 14.32; HRFAB-MS (thioglycerol+Na⁺ matrix) m/e ([M+Na]⁺) 1149.8790(100%), calcd 1149.8786.

To liquid NH₃ (ca. 8 mL) under N₂ at −78° C. was added Na° (20 mg), and the mixture was stirred for 2 min. To the blue solution was added the amine (18 mg, 0.016 mmol) in THF (1 mL), and the mixture was stirred for 40 min at −78° C. The reaction was quenched by addition of MeOH (4 mL). Ammonia was removed with a stream of N₂, and the solution was diluted with MeOH to 8 mL. The solution was concentrated under reduced pressure, and the residue was purified by column (SiO₂, CHCl₃:MeOH:NH₃—H₂O 1:0.4:0.02) to give 2 (7.3 mg, 53%) as a white solid. NMR ($^1$H, 5% CD₃OD in CDCl₃) δ 4.91 (d, J=4.0 Hz, 1H), 4.21 (m, 1H), 3.88 (m, 2H), 3.80 (dd, J=10.0, 3.5 Hz, 1H), 3.75 (m, 1H), 3.70 (dd, J=10.0, 3.5 Hz, 1H), 3.62-3.51 (m, 10H), 3.06 (dd, J=13.0, 7.5 Hz, 1H), 2.90 (dd, J=13.0, 4.0 Hz, 1H), 2.19 (t; J=8.0 Hz, 2H), 1.68-1.25 (m, 73H). 0.88 (t, J=7.0 Hz, 6H); NMR ($^{13}$C, 5% CD₃OD in CDCl₃) δ 174.36, 99.75, 75.17, 72.06, 70.84, 70.37, 70.22, 68.92, 67.31, 50.36, 42.40, 36.62, 33.02, 31.97, 29.83, 29.77, 29.74, 29.71, 29.70, 29.61, 29.46, 29.42, 25.90, 25.87, 22.73, 14.11; HRFAB-MS (thioglycerol+Na⁺ matrix) m/e ([M+Na]⁺) 879.7384(100%), calcd 879.7377.

EXAMPLE 5

Preparation of Compound 8

Dansyl chloride (1.5 mg, 0.0055 mmol) was added to a solution of 2 (4.5 mg, 0.005 mmol) in pyridine (1 mL), and the mixture was stirred for 5 h. The pyridine was removed in vacuo, and the product was purified chromatographically (SiO₂, 10% MeOH in CH₂Cl₂) giving a light yellow glass (3.4 mg, 60% yield). NMR ($^1$H, 5% CD₃OD in CDCl₃) δ 8.55 (d, J=9.0 Hz, 1H), 8.26 (d, J=8.5 Hz, 1H), 8.19 (dd, J=7.0, 1.5 Hz, 1H), 7.58-7.50 (m, 2H), 7.20 (d, J=7.5 Hz, 1H), 6.93 (d, J=8.5 Hz, 1H), 4.83 (d, J=2.5 Hz, 1H), 4.22 (m, 1H), 3.91 (m, 3H), 3.72 (m, 2H), 3.64-3.55 (m, 4H), 3.07 (m, 2H), 2.88 (s, 6H), 2.22 (br, 7H), 1.62-1.25 (m, 72H), 0.87 (t, J=7.0 Hz, 6H); NMR ($^{13}$C, 5% CD₃OD in CDCl₃) δ 174.45, 152.09, 134.62, 130.69, 130.10, 129.71, 129.36, 123.31, 118.91, 115.43, 99.68, 75.36, 72.41, 70.18, 69.55, 69.13, 69.03, 67.96, 50.42, 45.56, 43.28, 36.78, 33.14, 32.07, 29.93, 29.88, 29.85, 29.82, 29.80, 29.72, 29.57, 29.52, 25.96, 25.94, 22.84, 14.25; HRFAB-MS (thioglycerol+Na⁺ matrix) m/e ([M+Na]⁺) 1112.7867(100%), calcd 1112.7887.

EXAMPLE 6

Preparation of Compound 10

Ester 9 (9.4 mg, 0.02 mmol) was added to a solution of 2 (5.1 mg, 0.0059 mmol in pyridine (1 mL), and the mixture was stirred for 12 h. The pyridine was removed in vacuo, and the product was purified by column chromatography (SiO₂, 10% MeOH in CH₂Cl₂) giving a light yellow glass (3.7 mg, 53% yield). NMR ($^1$H, 5% CD₃OD in CDCl₃) δ 8.53 (d, J=9.0 Hz, 1H), 8.28 (d, J=8.5 Hz, 1H), 8.20 (dd, J=7.5, 1.2 Hz, 1H), 7.59-7.50 (m, 2H), 7.20 (d, J=7.5 Hz, 1H), 7.04 (d, J=8.5 Hz, 1H), 4.91 (d, J=3.0 Hz, 1H), 4.17 (m, 1H), 3.90 (dd, J=10.5, 4.5 Hz, 1H), 3.84 (m, 4H), 3.75 (dd, J=11.0, 4.5 Hz, 1H), 3.68-3.64 (m, 2H), 3.57-3.54 (m, 2H), 3.20 (dd, J=13.5, 5.5 Hz, 1H), 2.89 (s, 6H), 2.80 (m, 1H), 2.46-2.03 (m, 11H), 1.62-1.25 (m, 78H), 0.87 (t, J=7.5 Hz, 6H); NMR ($^{13}$C, 5% CD₃OD in CDCl₃) δ 175.38, 174.50, 152.04, 134.69, 130.52, 130.01, 129.72, 129.61, 128.46, 123.31, 118.98, 115.40, 99.71, 74.97, 72.45, 69.94, 69.01, 68.95, 68.03, 50.39, 45.54, 42.76, 42.61, 39.45, 36.57, 35.87, 32.79, 32.06, 29.85, 29.68, 29.50, 29.41, 28.97, 26.85, 26.00, 25.92, 25.49, 25.03, 24.77, 24.37, 22.82, 14.23; HRFAB-MS (thioglycerol+Na⁺ matrix) m/e ([M+Na]⁺) 1225.8741(100%), calcd 1225.8728.

EXAMPLE 7

Preparation of Compound 12

Ester 11 (6.6 mg, 0.018 mmol) was added to a solution of 2 (5.0 mg, 0.0058 mmol) in pyridine (1 mL), and the mixture was stirred for 12 h. The pyridine was removed in vacuo, and the product was purified by column chromatography (SiO₂, 10% MeOH in CH₂Cl₂) giving compound 12 as a clear glass (3.0 mg, 46% yield). NMR ($^1$H, 5% CD₃OD in CDCl₃) δ 8.36 (m, 1H), 7.89 (dd, J=8.0, 1.5 Hz, 1H), 7.81 (d, J=8.5 Hz, 1H), 7.64 (d, J=8.5 Hz, 1H), 7.18 (dd, J=8.5, 2.5 Hz, 1H), 7.01 (d, J=8.0 Hz, 1H), 6.86 (d, J=2.5 Hz, 1H), 4.89 (d, J=4.0 Hz, 1H), 4.19 (m, 1H), 3.92 (dd, J=10.0, 4.5 Hz, 1H), 3.82-3.38 (m, 9H), 3.22 (dd, J=13.5, 6.0 Hz, 1H), 3.19 (s, 6H), 2.65 (t, J=7.0 Hz, 2H), 2.34 (br, 5H), 2.18 (m, 2H), 2.05-2.08 (m, 2H), 1.65-1.23 (m, 72H), 0.87 (t, J=7.0-Hz, 6H); NMR ($^{13}$C, 5% CD₃OD in CDCl₃) δ 199.01, 174.46, 150.56, 138.06, 130.98, 130.42, 129.86, 126.43, 125.10, 124.35, 121.72, 116.49, 110.59, 105.36, 99.72, 84.07, 75.29, 72.47, 70.11, 69.23, 68.99, 68.69, 67.80, 60.06, 50.56, 40.54, 36.76, 33.62, 33.11, 32.07, 30.23, 29.86, 29.85, 29.81, 29.80, 29.71, 29.57, 29.51, 25.99, 22.83, 14.25; HRFAB-MS (thioglycerol+Na⁺ matrix) m/e ([M+Na]⁺) 1132.8484(100%), calcd 1132.8480.

EXAMPLE 8

Preparation of Compound 13

N-hydroxysuccinimidobiotin (5.9 mg, 0.017 mmol) and Et₃N (30 ul) were added to a solution of 2 (5.0 mg, 0.0058 mmol) in DMF(1.5 mL). The mixture was stirred for 12 h, and applied directly to an SiO₂ column. Elution with 10% MeOH in CH₂Cl₂ gave the product 13 as a clear glass (3.2 mg, 52% yield). NMR ($^1$H, Pyridine-d₅) δ 8.86 (m, 1H), 8.61 (d, J=9.0 Hz, 1H), 7.54-7.40 (m, 4H), 5.54 (d, J=4.0 Hz, 1H), 5.28 (br, OH), 4.66-4.61 (m, 2H), 4.56-4.50 (m, 3H), 4.41-4.31 (m, 6H), 4.23 (m, 1H), 3.92 (m, 1H), 3.27 (m, 1H), 3.16 (m, 1H), 3.0-2.85 (m, 10H), 2.55-2.44 (m, 6H), 2.32 (m, 1H), 1.96-1.50 (m, 20H), 1.32-1.26 (m, 44H), 0.87 (t, J=7.0 Hz, 6H); NMR ($^{13}$C, pyridine-d₅) δ 170.36, 169.46, 164.28, 101.41, 76.88, 72.57, 71.30, 71.21, 70.74, 70.10, 68.62, 62.41, 62.36, 60.57, 56.30, 56.13, 51.24, 41.22, 41.15, 36.86, 36.27, 34.52, 32.17, 30.89, 30.46, 30.23, 30.11, 29.98, 29.89, 29.85, 29.67, 29.12, 28.87, 28.53, 26.56, 26.50, 26.27, 26.16, 26.10, 24.85, 22.98, 14.33; HRFAB-MS (thioglycerol+Na⁺ matrix) m/e ([M+Na]⁺) 1105.8143(100%), calcd 1105.8153.

EXAMPLE 9

In Vivo Antitumor Assay

Experiment is performed with groups consisting of 6 female BDF₁ mice, 6 weeks old, B16 mouse melanoma cells (1×10⁶) are inoculated subcutaneously in the rear part of mice (day 0). On 1, 5, and 9 days after inoculation, a sample in a level of 0.1 mg/kg is administered to the tail vein in a dose of 0.2 ml/20 g/mouse. The volume of tumor in the subcutaneous rear partis measured on 8, 12, 16, and 20 days to determine the tumor growth inhibiting rate of each sample.

EXAMPLE 10

In Vivo Antiautoimmune Activity Assay

Representative compounds of the formulae herein are screened for antiautoimmune activity in a nonobese diabetic (NOD) mouse assay essentially as described in Wang, B.; Geng, Y.-B.; Wang, C.-R. *J. Exp. Med.* 2001, 194, 313-319, incorporated herein by reference.

EXAMPLE 11

In Vivo Antiautoimmune Activity Assay

Representative compounds of the formulae herein are screened for antiautoimmune activity in an experimental autoimmune encephalomyelitis MAE) assay essentially as described in Pal, E.; Tabira, T.; Kawano, T.; Taniguchi, M.; Miyake, S.; Yamamura, T. *J Immunol.* 2001, 166, 662-668, incorporated herein by reference.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Other embodiments are in the claims.

We claim

1. A compound of Formula (I):

(I)

wherein,
$R_1$ is —C(O)$R_{10}$, wherein $R_{10}$ is
  $C_1$-$C_{12}$ alkyl optionally substituted with;
$R_2$ is hydrogen;
$R_3$, $R_4$, $R_5$, $R_6$, and $R_7$ are each hydrogen;
$R_8$ is —(CH$_2$)$_x$CH$_3$;
$R_9$ is a linear or branched $C_3$-$C_{100}$ alkyl; and
x is 1-100.

2. The compound of claim 1 wherein x is 24 and $R_9$ n-tetradecyl.

3. A method of stimulating NKT cells comprising contacting an NKT cell with a compound of Formula (I) claim 1 and a CD1d protein.

4. A method of making a compound of Formula (I) claim 1 comprising: (i) converting a compound of Formula (III) to a compound of Formula (IV):

and (ii) contacting a compound of Formula (IV) with $R_1$-LG to afford a compound of Formula (I), wherein:
$R_1$ is —C(O)$R_{10}$, wherein $R_{10}$ is
  $C_1$-$C_{12}$ alkyl optionally substituted with carboxyl;
$R_3$, $R_4$, $R_5$, $R_6$, and $R_7$ are each hydrogen
$R_8$ is —(CH$_2$)$_x$CH$_3$;
$R_9$ is a linear or branched $C_3$-$C_{100}$ alkyl;
x is 1-100; and
LG is halo, —OSO$_2$R$_{16}$, B(OH)$_2$, or $R_{16}$ is alkyl, halo alkyl or aryl optionally substituted with alkyl, halo or nitro.

5. A pharmaceutical composition comprising a compound of Formula (I) in claim 1 and a pharmaceutically acceptable carrier.

6. The compound of claim 1, wherein $R_{10}$ is CH$_3$.

7. The compound of claim 6, wherein $R_9$ is $C_{14}$ alkyl.

8. The compound of claim 7, wherein $R_8$ is —(CH$_2$)$_{24}$CH$_3$.

9. The compound of claim 7, wherein $R_8$ is —(CH$_2$)$_{22}$CH$_3$.

10. The compound of claim 1, wherein $R_{10}$ is selected from —(CH$_2$)$_2$COOH, —(CH$_2$)$_3$COOH, and —(CH$_2$)$_4$COOH.

* * * * *

UNITED STATES PATENT AND TRADEMARK OFFICE
CERTIFICATE OF CORRECTION

PATENT NO. : 7,645,873 B2  Page 1 of 1
APPLICATION NO. : 10/550165
DATED : January 12, 2010
INVENTOR(S) : Savage et al.

It is certified that error appears in the above-identified patent and that said Letters Patent is hereby corrected as shown below:

Please amend the following paragraph beginning at Column 1 following the title with the following paragraph:

Col. 1, line 3: -- ~~A portion of the work described herein was supported by grant number AI53725 from the National Institutes of Health. The United States Government has certain rights in this invention.~~ This invention was made with government support under AI53725 awarded by the National Institutes of Health. The United States Government has certain rights to this invention. --

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,645,873 B2  Page 1 of 1
APPLICATION NO. : 10/550165
DATED : January 12, 2010
INVENTOR(S) : Savage et al.

It is certified that error appears in the above-identified patent and that said Letters Patent is hereby corrected as shown below:

Col. 2, line 11: "nitro, ammo," should read --nitro, amino,--

Col. 25, line 50, claim 1: "substituted with;" should read --substituted with carboxyl;--

Signed and Sealed this

Thirty-first Day of August, 2010

David J. Kappos
*Director of the United States Patent and Trademark Office*